US008855386B2

(12) United States Patent
Ioudovski et al.

(10) Patent No.: US 8,855,386 B2
(45) Date of Patent: Oct. 7, 2014

(54) REGISTRATION METHOD FOR MULTISPECTRAL RETINAL IMAGES

(75) Inventors: Alexei Ioudovski, Ottawa (CA); Alan Boate, Ottawa (CA)

(73) Assignee: Annidis Health Systems Corp., Ottawa, Ontario (CA)

( * ) Notice: Subject to any disclaimer, the term of this patent is extended or adjusted under 35 U.S.C. 154(b) by 64 days.

(21) Appl. No.: 13/574,662

(22) PCT Filed: Jan. 21, 2011

(86) PCT No.: PCT/CA2011/050038
§ 371 (c)(1),
(2), (4) Date: Jul. 23, 2012

(87) PCT Pub. No.: WO2011/088578
PCT Pub. Date: Jul. 28, 2011

(65) Prior Publication Data
US 2012/0300998 A1    Nov. 29, 2012

Related U.S. Application Data

(60) Provisional application No. 61/297,475, filed on Jan. 22, 2010.

(51) Int. Cl.
*G06K 9/00* (2006.01)
*G06K 9/32* (2006.01)
*A61B 3/00* (2006.01)

(52) U.S. Cl.
CPC .................................... *A61B 3/0025* (2013.01)
USPC .......................................... 382/128; 382/300

(58) Field of Classification Search
CPC ................... G06T 2207/30041; G06T 7/0014; H04N 19/00587; H04N 19/00593
USPC .................................................. 382/128, 300
See application file for complete search history.

(56) References Cited

U.S. PATENT DOCUMENTS

2003/0088165 A1    5/2003  Smith et al.
2007/0002276 A1    1/2007  Hirohara et al.
(Continued)

OTHER PUBLICATIONS

Can et al., "A featured-Based, Robust, Hierarchical Algorithm for Registering Pairs of Images of the Curved Human Retina," IEEE Transactions on Patter Analsis and Machine Intelligence, vol. 24, No. 3., Mar. 2002.*

(Continued)

*Primary Examiner* — Amir Alavi
*Assistant Examiner* — Kenny Cese
(74) *Attorney, Agent, or Firm* — Mukundan Chakrapani; Borden Ladner Gervais LLP

(57) ABSTRACT

A method for performing registration of multispectral retinal images. Corresponding cross-over points and bifurcation points of blood vessel in an eye are identified in a fixed image and in an offset image. The relative displacement of each point, between the images, is calculated. Based on these relative displacements, the offset of each pixel in the offset image is interpolated and the offset image is transformed into a corrected (distorted) image. Such an image can be used to assess the health of the eye. Further, a fixed image and a offset image of an eye are divided in a tile pattern. The relative displacement of each tile of the offset image with respect to the corresponding tile in the fixed image is calculated. An offset for each tile is calculated and the offset image is corrected as a function of those offsets.

4 Claims, 6 Drawing Sheets

(56) References Cited

U.S. PATENT DOCUMENTS

2008/0007691 A1    1/2008  Mihashi et al.
2009/0316112 A1*  12/2009  Neal et al. .................... 351/246

OTHER PUBLICATIONS

International Patent Application No. PCT/CA2011/050038, International Search Report dated Apr. 8, 2011, 7 pages.
Can et al., "A Feature-Based, Robust, Hierarchical Algorithm for Registering Pairs of Images of the Curved Human Retina", IEEE Transactions on Pattern Analysis and Machine Intelligence, vol. 24. No. 3, Mar. 2002, pp. 347-364.
Haber et al., "A Multilevel Method for Image Registration", SIAM J. Sci. Comput., vol. 27, No. 5, Feb. 3, 2006, pp. 1594-1607.
Rui et al., "An Overview of Medical Image Registration", Proceedings of the Fifth International Conference on Computational Intelligence and Multimedia Applications, Sep. 27-30, 2003, pp. 1-6.
Ibanez et al., "Bayesian detection of the fovea in eye fundus angiographies", Pattern Recognition Letters (20), Feb. 1999, pp. 229-240.
Ritter et al., "Registration of Stereo and Temporal Images of the Retina", IEEE Transactions on Medical Imaging, vol. 18, No. 5, May 1999, pp. 404-418.
Wachowiak et al., "High-Performance Medical Image Registration Using New Optimization Techniques" IEEE Transactions on Information Technology in Biomedicine, vol. 10, No. 2, Apr. 2006, pp. 344-353.
Zhang et al., "Automatic Retinal Image Resgitration Based on Blood Vessels Feature Point", Proceedings of the First International Conference on Machine Learning and Cybernetics, Beijing, Nov. 4-5, 2002, pp. 2010-2015.
Chaudhuri et al., "Detection of Blood Vessels in Retinal Images Using Two-Dimensional Matched Filters", IEEE Transactions on Medical Imaging, vol. 8, No. 3, Sep. 1989, pp. 263-269.
Radke et al., "Image Change Detection Algorithms: A Systematic Survey" IEEE Transactions on Image Processing, vol. 14, No. 3, Mar. 2005, pp. 294-307.
European Patent Application No. 11734308.7, Extended European Search Report dated May 21, 2014, 6 pages.

* cited by examiner

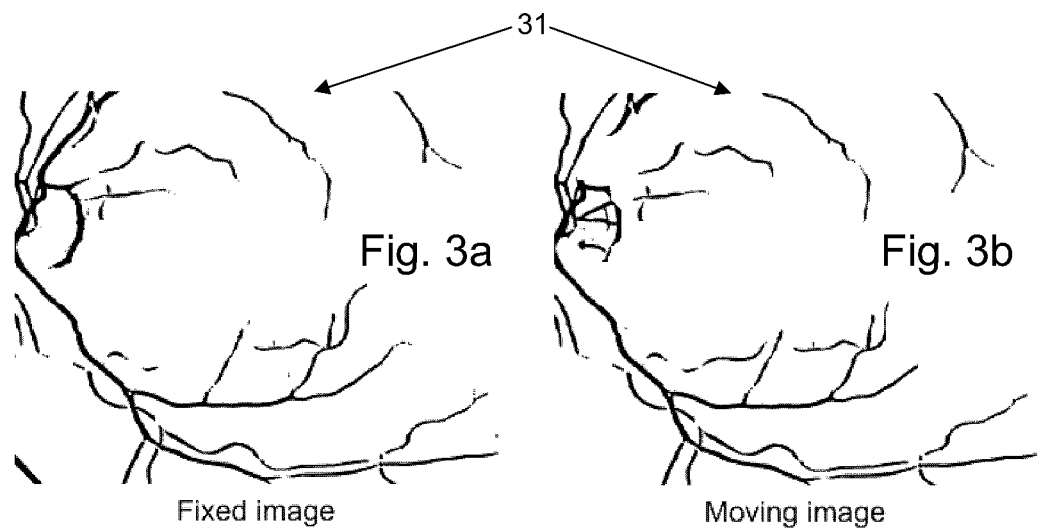
Fig. 3a  Fixed image
Fig. 3b  Moving image
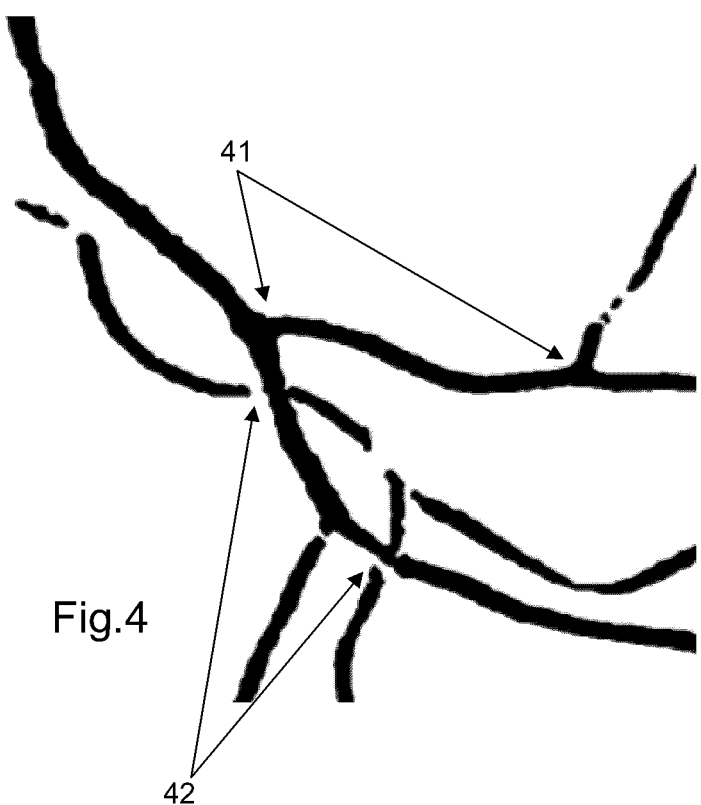
Fig. 4

REGISTRATION METHOD FOR MULTISPECTRAL RETINAL IMAGES

FIELD

The present invention relates generally to a method for imaging the retinal fundus. More particularly, the present invention relates to a method for registration of multispectral retinal fundus images.

BACKGROUND

The fundus of the eye, or retina, is a complex layered structure arranged in an approximately spherical shape at the back of the eyeball. It contains the light sensing rods and cones that enable vision. It is nourished by oxygenated blood supplied through arterioles and removed through venules. The nerve impulses from the rods and cones are directed to the brain through the optic nerve on the fundus, which corresponds to the blind spot.

Direct visual observation of the retinal fundus can be accomplished using an ophthalmoscope, an instrument that has been around in various forms for over 150 years. The ophthalmoscope employs a light source, means for coupling the light into the eye through the pupil, and means for collecting light reflected back from the fundus and presenting an image of the fundus to the observer. The eye responds to continuous light by constricting the pupil size and so reducing the amount of light available to form the image of the fundus. For this reason, the eye pupil may have to be chemically dilated, using a mydriatic, in order to facilitate imaging of the fundus.

A fundus camera is similar to the ophthalmoscope but provides a permanent record of the fundus image in the form of a photograph. It also enables the use of a short, powerful flash of light to replace the continuous light required for the ophthalmoscope, and so sometimes avoiding the need for a mydriatic. The fundus camera uses an electronic image sensor such as a charge-coupled device (CCD) and the image can be stored electronically. The image may also be displayed on a monitor or printed out as a photograph.

The fundus image is dominated by the appearance of the optic nerve and the vascular structure of arterioles and venules. It is substantially of the colour red, this coming from the blood, with some regions having an orange or yellow bias. The ophthalmologist is able to use the fundus image to aid in the diagnosis of the health of the eye. Thorough diagnosis requires the use of a battery of other oculometric instruments in addition to the fundus camera.

The fundamental limitations of fundus imaging as a diagnostic tool are rooted in the subjective nature of the image evaluation and in the substantial variations in the image that result from the uncertainties of many of the parameters that are integral to the imaging process and presentation.

The colour perception of the human eye is variable. No two people perceive the same colour image in the same way, and in some cases, one may suffer from a form of colour-blindness, commonly an inability to distinguish red from green. As there is only a very minor blue component in a retinal image, red-green colour blindness effectively removes all colour information, and a technician having such colour blindness cannot properly assess a retinal image. The colour perception of the human eye is also conditioned by the intensity and spectrum of the environmental lighting; the background illumination may come from daylight, some form of fluorescent lighting, or incandescent lighting.

Similarly, the colour presentation of images using photographs or electronic displays is variable. Any photograph or display is limited by the gamut of colours enclosed by the specific three primary colours employed. The process and manufacturing tolerances will result in a spread from one photograph or display to another, which will be compounded by aging effects and the impact of environmental influences such as temperature.

Visual observation of the fundus is essentially a rudimentary form of multispectral imaging where the three colour channels correspond to those of the observing eye. The spectral sampling locations and widths of the three visual colour channels do not necessarily correspond with those that would be chosen in an optimal fashion determined by the reflection characteristics of the retina associated with specific retinal diseases or defects.

Potentially important information contained in small variations of the intensity or brightness of the image may be lost where the dynamic range of the display is limited. Such variations may be hidden in a white-out region or a darkened region of the retinal image, or simply missed as the human eye is limited in its ability to discern minor changes in intensity or brightness across the image.

The limitations of the display and the perception thereof are further compounded by the uncertainties associated with generating the image. The illumination source intensity and optical spectrum can vary from camera to camera, from time to time, and with the age of the instrumentation employed. This will result in concomitant variations in apparent image brightness. The sensitivity of the image sensor, be it film or electronic (e.g., a CCD), can also vary from unit to unit. This will also result in concomitant variations in apparent image brightness. The optical transmission efficiency of the eye is not always high, especially in the presence of cataracts. The transmission efficiency will also vary across the optical spectrum. This will result in concomitant variations in apparent image brightness and colour. The amount of illumination that is reflected from the retina and that returns to the imaging apparatus is strongly dependent on the size of the pupil. As the size of the pupil varies greatly from person to person and with environmental lighting conditions, this will further result in concomitant variations in apparent image brightness.

Further, the reflectivity of the retina can be strongly dependent on the ethnicity of the person, as a consequence of the different concentrations of melanin. People of African ethnicity have higher melanin concentrations resulting in low retinal reflectivity, which can lead to dark retinal images that are difficult to interpret.

Furthermore, during retinal fundus imaging, a patient is typically required to fixate on a target as one or more images of the retina are obtained. As the eye can move between images, no two images are likely identical and common structure between any two images can be several hundreds of pixels apart.

In addition, the retina is not an ideal spherical surface, and can be slightly deformed during a cardiac event (the pressure wave from a heart beat may induce a mechanical or reflective change and hence affect the perceived vessel position). This factor is of greater importance when the inter-study (examinations over time to establish longitudinal trends) analysis is performed Ophthalmologists need to carefully track the progression of the retinal health problems of their patients in order to prescribe the most appropriate course of treatment. For this purpose, they carry out examinations over time to establish longitudinal trends. However, because of the variations and uncertainties listed above, the utility of fundus cameras for longitudinal monitoring is severely limited.

It is, therefore, desirable to provide a fast and efficient method and apparatus for registration of multispectral retinal images.

SUMMARY

The present invention relates to a method for performing registration of multispectral retinal images.

In a first aspect of the invention, there is provided a method to register retinal images. The method comprises determining a first tracing of a blood vessel in a first retinal image acquired at a first optical wavelength; determining a second tracing of the blood vessel in a second retinal image acquired at a second optical wavelength; and identifying features common to the first tracing and the second tracing, to obtain identified features. The method further comprises determining a feature displacement vector for each identified feature of the second tracing with respect to a corresponding identified feature of the first tracing; calculating, in accordance with the feature displacement vectors, a pixel displacement vector for pixels of the second retinal image; and transforming the second retinal image in accordance with the pixel displacement vectors to obtain a transformed second image registered to the first retinal image.

Calculating, in accordance with the feature displacement vectors, the pixel displacement vector for pixels of the second retinal image can include interpolating feature displacement vectors.

The identified features can include at least one of bifurcation points and crossover points.

The method can further comprise storing the transformed second image in a tangible computer-readable memory.

Determining the first tracing and the second tracing can be preceded by acquiring the first retinal image at the first optical wavelength and the second retinal image at the second optical wavelength. The first retinal image and the second retinal image can show an optical nerve disk. Acquiring the first retinal image at the first optical wavelength and the second retinal image at the second optical wavelength can include monitoring a pulse characteristic of a patient whose retina is to be imaged, and acquiring the first retinal image and the second retinal image in accordance with the pulse characteristic.

In a second aspect of the invention, there is provided a tangible computer-readable medium having stored thereon statements and instructions to enable a computer to perform a method of registering retinal images. The method comprises determining a first tracing of a blood vessel in a first retinal image acquired at a first optical wavelength; determining a second tracing of the blood vessel in a second retinal image acquired at a second optical wavelength; and identifying features common to the first tracing and the second tracing, to obtain identified features. The method further comprises determining a feature displacement vector for each identified feature of the second tracing with respect to a corresponding identified feature of the first tracing; calculating, in accordance with the feature displacement vectors, a pixel displacement vector for pixels of the second retinal image; and transforming the second retinal image in accordance with the pixel displacement vectors to obtain a transformed second image registered to the first retinal image.

Calculating, in accordance with the feature displacement vectors, the pixel displacement vector for pixels of the second retinal image can include interpolating feature displacement vectors. The identified features can include at least one of bifurcation points and crossover points.

The method can further comprises storing the transformed second image in a computer-readable memory. Determining the first tracing and the second tracing can be preceded by acquiring the first retinal image at the first optical wavelength and acquiring the second retinal image at the second optical wavelength. The first retinal image and the second retinal image can show an optical nerve disk. Acquiring the first retinal image at the first optical wavelength and the second retinal image at the second optical wavelength can include monitoring a pulse characteristic of a patient whose retina is to be imaged, and acquiring the first retinal image and the second retinal image in accordance with the pulse characteristic.

In a third aspect, the invention provides a method to register retinal images. The method comprises: dividing a first retinal image acquired at a first optical wavelength into first image portions; dividing a second retinal image acquired at a second optical wavelength into second image portions, each second image portion having a corresponding first image portion; determining a deformation vector for each second image portion with respect to its corresponding first image portion; identifying second image portions that have a deformation vector that fails a pre-determined criteria, to obtain identified second image portions; calculating, for each identified second image portion, an interpolated deformation vector in accordance with deformation vectors of neighbour second image portions; substituting, for each identified second image portion, its deformation vector with its corresponding interpolated deformation vector; and registering second image portions to their corresponding first image portions in accordance with deformation vectors that pass the pre-determined criteria and in accordance the interpolated deformation vectors.

Calculating, for each identified second image portion, the interpolated deformation vector in accordance with the deformation vectors of the neighbour second image portions can include performing a bi-linear interpolation in accordance with the deformation vectors of the neighbour second image portions.

In a fourth aspect, there is provided a tangible computer-readable medium having stored thereon statements and instructions to enable a computer to perform a method of registering retinal images, the method comprising: dividing a first retinal image acquired at a first optical wavelength into first image portions; dividing a second retinal image acquired at a second optical wavelength into second image portions, each second image portion having a corresponding first image portion; determining a deformation vector for each second image portion with respect to its corresponding first image portion; identifying second image portions that have a deformation vector that fails a pre-determined criteria, to obtain identified second image portions; calculating, for each identified second image portion, an interpolated deformation vector in accordance with deformation vectors of neighbour second image portions; substituting, for each identified second image portion, its deformation vector with its corresponding interpolated deformation vector; and registering second image portions to their corresponding first image portions in accordance with deformation vectors that pass the pre-determined criteria and in accordance the interpolated deformation vectors.

Calculating, for each identified second image portion, the interpolated deformation vector in accordance with the deformation vectors of the neighbour second image portions can include performing a bi-linear interpolation in accordance with the deformation vectors of the neighbour second image portions.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 3a and 3b show binary images of a blood vessel structure in a fixed image and in an offset image respectively.

FIG. 4 shows details of a blood vessel structure in a binary image.

DETAILED DESCRIPTION

Generally, the present invention provides a method and apparatus for the registration of multispectral retinal images.

Images captured at various wavelengths by present fundus cameras vary in intensity, noise levels and appearance of features such as blood vessels (arterioles and venules). Conventional methods based on similarity of the optical flow in image pairs fail when differences in brightness, contrast and signal-to-noise ratio differ significantly. Also, registration methods based on extraction of blood vessel structures are not efficient when applied to multispectral images because blood vessels cannot be extracted and matched reliably in multispectral images. Such differences make automated image alignment, or registration, a computationally challenging task.

Further, such images acquired at various wavelengths by present fundus cameras may differ in scale due to different working distances and magnification at different wavelengths.

Previously, attempts have been made to register or align retinal photographs to compare retinal images obtained during one session or those obtained over time to develop a patient profile and to monitor, for example, progression of a disease. In these attempts, the retinal images are typically obtained with white light illumination or with light having the same optical spectrum (temperature) illuminating the retina in all images.

Figure 1:
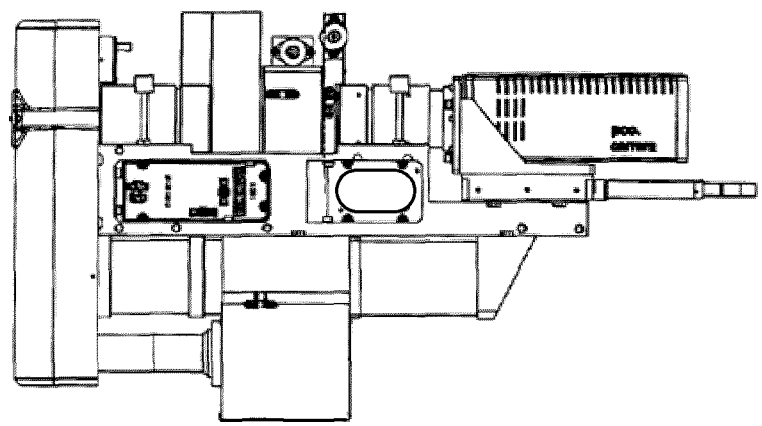
FIG. 1 shows a fundus camera.
Figure 2:
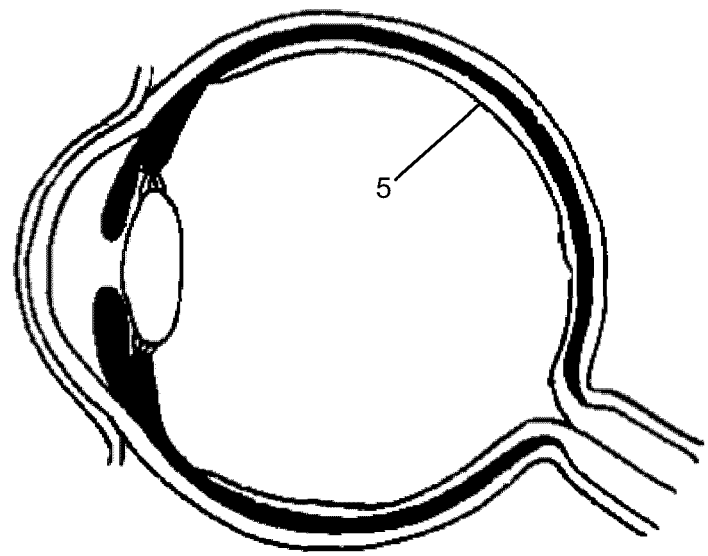
FIG. 2 shows an Internal structure of an eye.

As for retinal fundus imaging systems, such as the system shown at FIG. 1, many distinct, successive images of the retina can be obtained. The retina is a quasi-spherical surface with several layers of structure on the inside surface of this sphere. FIG. 2 shows a cross-sectional view of an eye, which has such a quasi-spherical surface 5. Light at each wavelength can reflects differently from different layers within the eye structure leading to certain regions appearing bright in some images taken at a first wavelength while the same regions appear darker in other images acquired at a second wavelength. Thus, while there is commonality between images to an extent, there are also major differences.

The problem of registering or aligning multiple images is further compounded by the movement of the eye between image capture events, the distortion caused by the quasi-spherical surface of the retina being projected onto a flat image plane of the imaging device, such as a CCD camera, and the flexure of the retina in accordance with periodic variations in blood pressure caused by the heartbeat.

FIGS. 3a and 3b respectively show a binary fixed image and a binary offset image from of a blood vessel structure. For the purpose of the present disclosure, an offset image can also be referred to as a distorted image or a moving image, that is, as an image being displaced in various directions, at various locations, with respect to a reference image (e.g., the fixed image). Any image of the retina can be used as the fixed image, while any other image of the retina can be used as the offset image. The choice of the fixed and offset images can be based on the quality/contrast of the image. As is apparent from FIGS. 3a and 3b, features visible in FIG. 3a are absent from FIG. 3b. The feature labelled 31 in FIGS. 3a and 3b indicates the vicinity of the optical nerve head or disk.

FIG. 4 shows details of a blood vessel structure in a binary image. Shown in FIG. 4 are bifurcation (BF) points 41 and crossover (CO) points 42.

Figure 5:
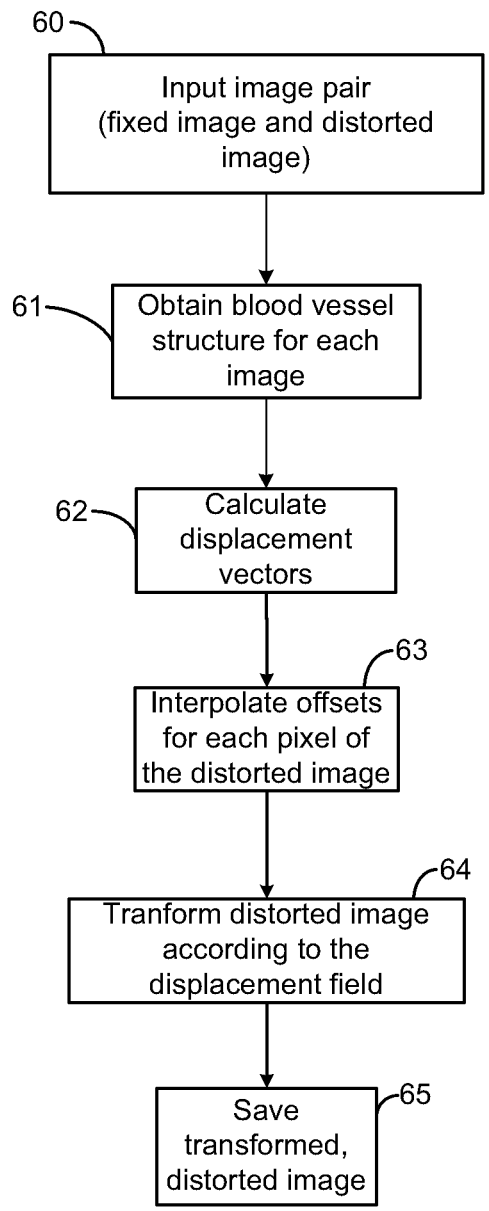
FIG. 5 shows an example of a method of the present invention.

In accordance with an aspect of the present invention, there is provided a method of registration of multispectral images. An example of an image processing method of the present invention is shown at FIG. 5. Processing steps can include: 60—input of image pair, each image of the pair having been acquired at a different optical wavelength, 61—obtaining the blood vessel structure or tracing (e.g., tree structure) in each image (for example, to determine features such as crossover and bifurcation points) 62—calculation of the displacement vectors for selected crossover and bifurcation points (features), followed by 63—interpolation of displacement vectors for pixels (e.g., for each pixel) of the offset image. Once the transformation field (displacement vectors for the pixels) is obtained, the transformation, at step 64 is applied to the offset image to obtain a transformed, distorted image and to align it with the fixed image. At step 65, the distorted, transformed image can be saved.

Obtaining the blood vessel structure can comprise locating (identifying) blood vessel structures in each image using heuristic knowledge (that is, by using a priori knowledge) of the eye, and the specific intensity and contrast features of blood vessels as they appear at various wavelengths (in various images). Such specific features are the result of different reflectance and scattering of light at different wavelengths, and are due to the fact that blood vessels appear in a different way at different depths. The purpose of extracting the blood vessel maps with their tree-like structures from each of the image in a sequence is to identify a set of corresponding points in each of the images.

Figures 6A, 6B:
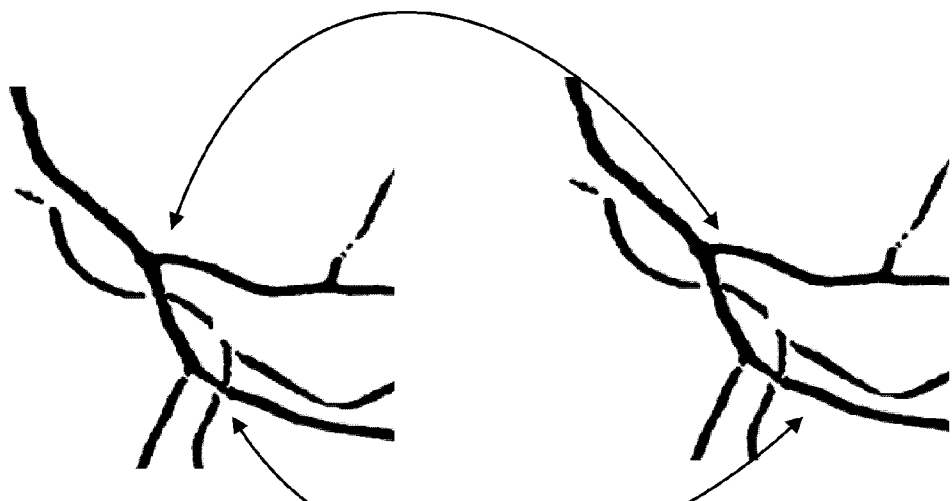
FIGS. 6a, 6b, 6c and 6d show analysis of bifurcation and crossover points.
Figures 6C, 6D:
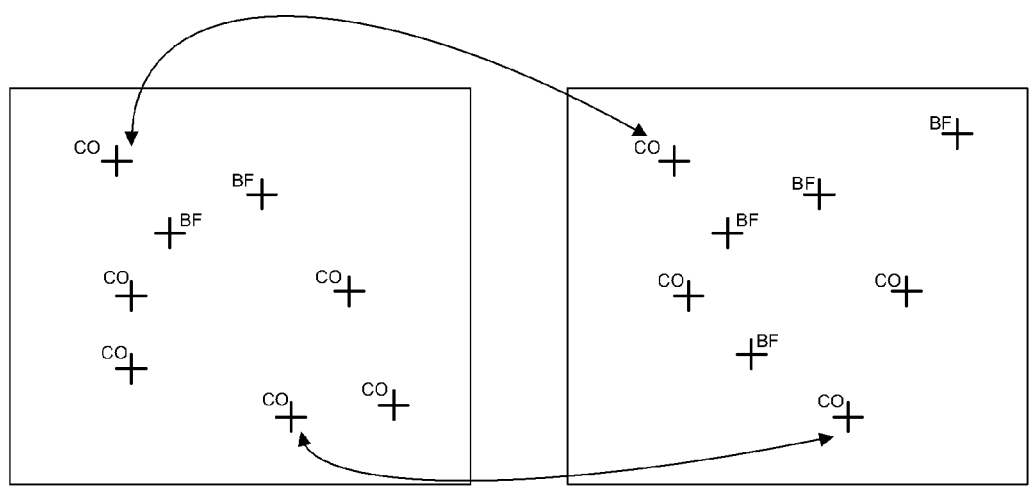

With reference, once again to FIG. 4, when the blood vessel map is examined and a bifurcation point 41 (BF) or a crossover point 42 (CO) is found, the decision about whether the point is a bifurcation point or a crossover point can be based on the information in the neighbourhood of the point, in the current image and in an image captured at a different wavelength. The exemplary image shown in FIG. 4, which shows a blood vessel structure, was processed to emphasize the blood vessels. Distance between such points (BF and CO points) can be less than an offset between images, so the point type (bifurcation or crossover) as an attribute can be important to find the correspondence between two point sets. An example of corresponding points is shown at FIGS. 6a and 6b, and, 6c and 6d. The crosses in FIGS. 6c and 6d represent corresponding points in a fixed image (FIG. 6c) and in an offset image (FIG. 6d). Also, the same bifurcation or crossover points might not be found in all images, as is apparent from the example shown at FIGS. 6c and 6d. This means that the number of BF and CO points in each image can be different. As such, the point type (bifurcation or crossover) can be an additional valuable parameter for establishing correspondences between point sets in image pairs.

The resulting blood vessel trees with determined bifurcations and crossovers points are independent of light or dark vessels in the images. Two sets of corresponding points (FIG. 6c and FIG. 6d) are generated for each of the images in an image pair. The two point sets can be used to determine a displacement vector field that describes an elastic transformation between images (between the "fixed" and "displaced" images in a pair). Each corresponding pair of points represents a displacement vector with the starting point in the "fixed" image and the end point in the "distorted" image.

The present exemplary method can be represented as projecting the distorted image on to a sheet of rubber and then using the displacement vector map to stretch the rubber in places that make the blood vessel structures of the distorted image align with those of the fixed image.

It can be reasonably assumed that if the vessel structures between retinal images are aligned, the rest of the retinal structures are also aligned. It is to be noted that while the vessel structure may shift during a cardiac pulse event (the pressure wave from the heart beating induces a physical and reflective change and hence affects the perceived vessel position); a pulse sensor operationally connected to the imaging system can be used to ensure that all images are obtained at the same point in the cardiac pressure wave event. That is, the images are can be acquired in accordance with the pulse characteristic of the patient whose retina is being imaged.

Once the displacement vector field is known, it is interpolated for the whole image using known 2-dimensional second or third order interpolation techniques. The result of such interpolation is a displacement vector field that corresponds to each pixel of the image, i.e., a displacement vector is defined for each pixel of the image.

After the displacement vector field for the entire displaced image is obtained, it is applied to the displaced image to obtain a new image (transformed, distorted image) that is in alignment with the fixed image. The fixed image and the transformed, distorted image can the be used by an eye specialist to assess the health of the eye.

This process is repeated for all images in a sequence. Images are registered either to each other or to an image that is chosen as a reference image. For example, if an image captured at 620 nm is chosen as a reference image, then the rest of the images can be registered to it (yellow to red, green to red, cyan to red and so on). Or, alternatively, images can be registered in a sequential manner (yellow to red, green to yellow, cyan to green and so on). Colors in this example are for illustrative purposes only. Each image is characterized by the wavelength at which it was acquired.

The method of registration of multispectral images described herein has successfully registered retinal image sets that the conventional registration algorithms, such as those in the Insight Segmentation and Registration Toolkit (ITK toolkit) failed to register.

This method can be further applied to register image sets taken several weeks/months/years apart. Furthermore, this method can be applied to register image sets that only partially overlap to generate a wider field of view image or a mosaic.

With respect to blood vessel tracing, it can start in the areas where blood vessels have high contrast, for example, in the vicinity of the optical nerve head or disk 31 (FIGS. 3a and 3b). The optical disk appears as a high intensity area and is clearly visible in all wavelengths. The optical disk can be used as a reference point from where blood vessels are traced. It is also used for an approximate alignment of images to minimize the search area which will be described later.

Each captured image can include an ordered set of pixels each of which is characterized by a number proportional to the quantity of captured photons within the pixel, i.e. the intensity. The binary image is a derivative of the original (gray scale) image intended to show only characteristic structure contours such as veins and arteries. However, in some areas of the binary images the blood vessels can be "broken", and appear as "dashed" curves. In order to find the correct tracing path when a break point is reached, the corresponding original gray scale image can be used to link the break point (in the binary image) with the continuation of the blood vessel, i.e., with another segment in the binary image. The selection of an appropriate candidate in the vicinity of the break point is based on the intensity of the original gray scale image.

Blood vessel tracing can be based on the intensity of the original gray scale image. From a given starting pixel, the next pixel on the blood vessel is traced in a direction that corresponds to the lowest intensity (blood vessels are darker than the background). Once the bifurcation 41 or a crossover point 42 (FIG. 4) is detected, the decision about the direction to follow is based on the analysis of pixel intensity in the neighbourhood of the bifurcation or crossover point. Each direction is given a weight according to contrast in that direction relative to the background. When all weights are below a pre-determined threshold, then the image of a different wavelength is used to make a decision about the direction. At the initial step all images are processed and portions of the blood vessel trees are generated for each of the images. Blood vessel trees and their bifurcation and crossover points are stored. At the initial step each unclassified point (crossover or bifurcation) is flagged as "unknown".

Once the set of blood vessel trees is obtained (step 61, FIG. 5), the sets of points of the image pair are passed to a displaced vector field interpolation module to perform step 63 shown in the example of FIG. 5.

Subsequently, a decision is made based on the spatial distribution of successfully extracted and classified points. If the number of such points is insufficient, or they are all clustered in a relatively small area then the image set is used for expanding each blood vessel tree (structure) further. The decision about the point type is based on the information in the current image and in an image that has venules or arteries with higher contrast. The analysis is performed on the image intensity in the neighbourhood of the non-classified point. The search area is minimized because the images were roughly aligned using the optical disk, and the classified points from the previous step if they are available.

The iterative steps can be repeated until a suitable spatial distribution of the classified bifurcation and crossover points is achieved. Then the displaced image in an image pair is subjected to the transformation according to the displaced vector field obtained from the last iteration (step 64 in example of FIG. 5).

As mentioned above, the retinal images captured at different moments in time and/or at different wavelengths, need to be aligned because of such factors as scale (varying magnification of the optical system at different wavelengths), translation (a shift in both X and Y direction), rotation (due to patient's head movement), and warping (at different times of a cardiac cycle). Conventional methods are based on similarities of features in the fixed and displaced images. However, those conventional methods are based on complex transformation models that are not suitable for clinical, real-time applications.

In a second embodiment of the present invention, the geometric image transformation from a fixed to a displaced image is presented as a piecewise linear approximation of a two-dimensional transformation (deformation) field (displacement vector field).

As was mentioned above, the deformation of the retina between image acquisitions due to the cardiac pulse may cause warping of images in some areas. The deformation field can be presented as a relatively smooth function of X,Y coordinates of the image. In this case a piecewise linear approximation of the deformation field can simplify the processing significantly. In other words, the deformation field can be presented as a set of displacement vectors at regular intervals at nodes on a 2-dimensional grid.

Figure 7A:
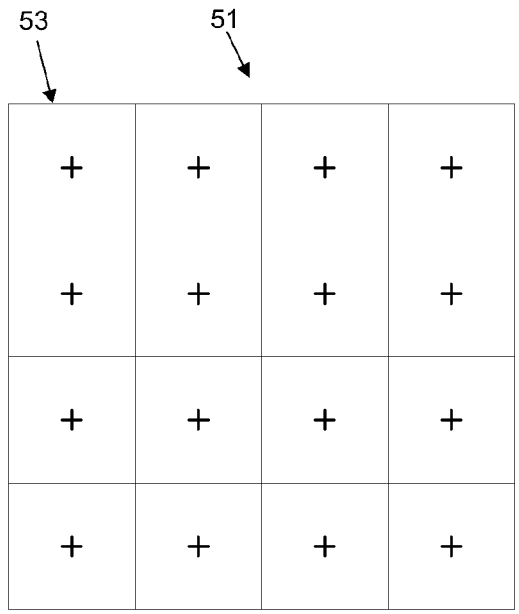
FIGS. 7a and 7b show image tiles of a fixed image and of an offset image respectively.
Figure 7B:
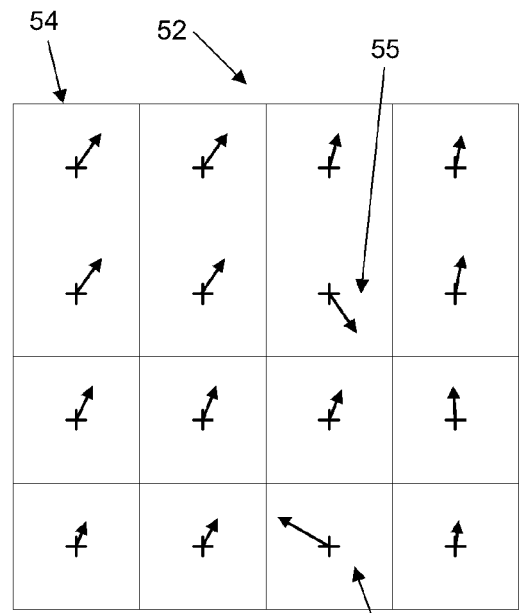

With reference to FIGS. 7a and 7b, the fixed image 51 and displaced image 52 are presented as sets of tiles 53 and 54. The size of the tiles is defined by the smoothness of the transformation field. The advantage of such approach is that if the transformation field is relatively smooth and it can be sufficient to represent a typical image as a set of 4×4 tiles while the number of tiles may be increased in cases when the deformation due to warping varies significantly across the images. Also, tiles may partially overlap to increase the robustness of this registration method; however, this leads to an increase in the processing time proportionally to the amount of overlap.

Figure 8:
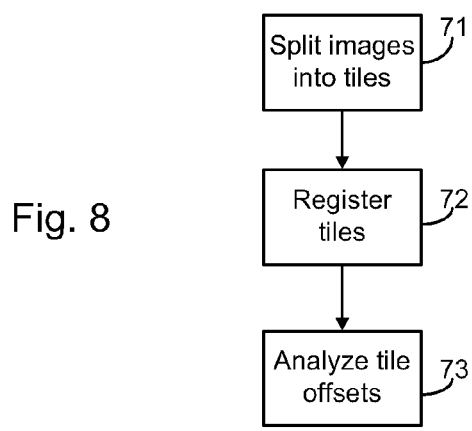
FIG. 8 shows another example of the method of the present invention.

With reference to FIG. 8, each image is split into tiles (71), each tile from the fixed image is aligned (registered) with the corresponding tile of the displaced image (72) using a conventional correlation-based method, for example, one of several rigid (calculation of X, Y offsets only) registration methods described in The ITK Software Guide. Subsequently, an analysis of the tile offset can be performed (73). Registration results (X, Y offsets) for each tile are stored for further processing. As will be described below, outliers can be deleted.

Rigid registration methods rely on the presence of distinctive features in image pairs such as blood vessels or other features that are significantly different in intensity and contrast.

Figure 9A:
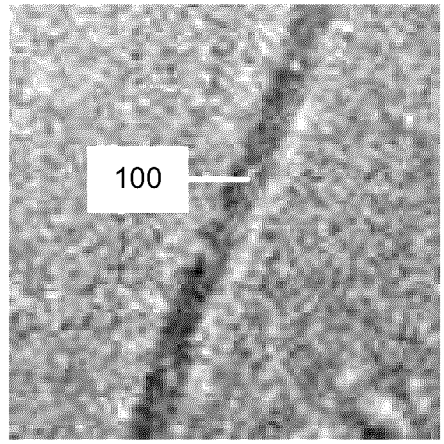
FIGS. 9a and 9b show a fixed image and an offset image of a blood vessel respectively.
Figure 9B:
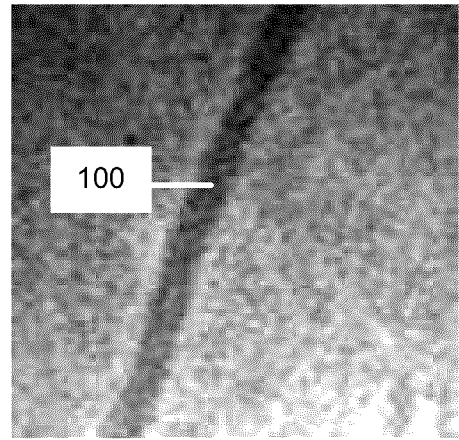

However, such features may not be present in all areas of the retinal images. Moreover, in some areas the features can be anisotropic in appearance thus making the process of finding the best match non-robust in presence of noise as shown in FIGS. 9a and 9b. Thus, with reference to FIGS. 7a and 7b, it may be necessary to process the offsets (displacement vectors) and delete the so called "outliers" 55 and 56, i.e. the displacement vectors that do not match (in intensity, direction, or both intensity and direction) with most of the displacement vectors. The process of deleting outliers is based on the assumption that the transformation field is relatively smooth. In the example of FIGS. 7a and 7b we have a set of 16 X,Y offsets for tiles in the displaced image.

Histograms of offsets can be generated separately for X and Y offsets, and the median value for X offsets and the median value for Y offsets can be calculated. Outliers can be identified as the ones that exceed a pre-determined threshold value from the median values of X and Y offsets. The next step can be to replace the deleted values (outlier values) with the interpolated values between adjacent correct values using bi-linear interpolation between the values above, below, on top and at the bottom of the deleted offset. At the boundary tiles (border tiles), only the existing correct offsets within the image boundaries are used.

Figure 10:
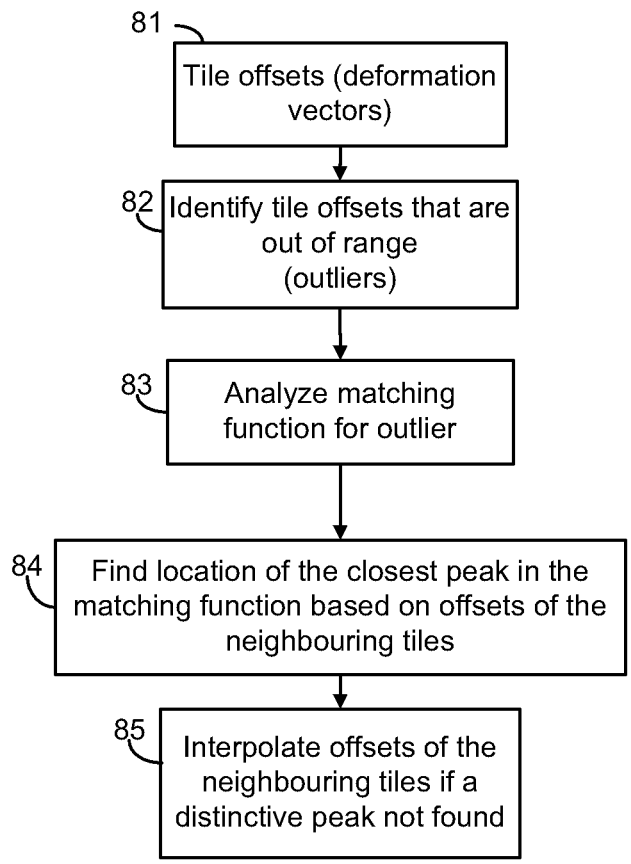
FIG. 10 shows yet another example of the method of the present invention.

Another approach is shown at FIG. 10. This approach is based on the analysis of two-dimensional matching functions between corresponding tiles in fixed and offset images. When two images contain an anisotropic structure, for example, a line 100 as shown in FIGS. 9a and 9b, the matching function will have a ridge along the line 100. The best match can be found by following the center of the ridge and comparing coordinates of the current tracing location with the coordinates of adjacent displacement vectors. Such approach eliminates the uncertainty due to the anisotropic nature of image data in both tiles.

Finally, the displacement vector field is produced and passed to the interpolation module as described above to generate the transformation field for the full image.

With respect to the exemplary method shown at FIG. 10, at step 81, the tile offsets are determined; at step 82, the tile offsets that are out of range (outliers) are identified; at step 83, an analysis of a matching function for outliers is performed; at step 84, the location of the closest peak in the matching function is determined; and, at step 85, the offsets of neighbour tiles are interpolated if a distinctive peak is not found.

In this embodiment, the displacement vector field is defined at regular intervals on a 2D grid, while in the first embodiment the displacement vector field is defined at the bifurcation and cross-over points in the blood vessel structure.

A system comprising a camera for recording retina images at different wavelengths and at different times, can be operationally connected to a computer having a memory, to store the images, and an image processing module, to perform the method of the present invention.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or computer to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments of the present invention are intended to be examples only. Alterations, modifications and variations may be effected to the particular embodiments by those of skill in the art without departing from the scope of the invention, which is defined solely by the claims appended hereto.

The invention claimed is:

1. A method to register retinal images, the method comprising:
    dividing a first retinal image acquired at a first optical wavelength into first image portions;
    dividing a second retinal image acquired at a second optical wavelength into second image portions, each second image portion having a corresponding first image portion;
    determining a deformation vector for each second image portion with respect to its corresponding first image portion;
    identifying second image portions that have a deformation vector that fails a pre-determined criteria, to obtain identified second image portions;
    calculating, for each identified second image portion, an interpolated deformation vector in accordance with deformation vectors of neighbour second image portions;
    substituting, for each identified second image portion, its deformation vector with its corresponding interpolated deformation vector; and
    registering second image portions to their corresponding first image portions in accordance with deformation vectors that pass the pre-determined criteria and in accordance the interpolated deformation vectors.

2. The method of claim 1 wherein calculating, for each identified second image portion, the interpolated deformation vector in accordance with the deformation vectors of the neighbour second image portions includes performing a bi-linear interpolation in accordance with the deformation vectors of the neighbour second image portions.

3. A non-transitory computer-readable medium having stored thereon statements and instructions to enable a computer to perform a method of registering retinal images, the method comprising:
    dividing a first retinal image acquired at a first optical wavelength into first image portions;
    dividing a second retinal image acquired at a second optical wavelength into second image portions, each second image portion having a corresponding first image portion;
    determining a deformation vector for each second image portion with respect to its corresponding first image portion;
    identifying second image portions that have a deformation vector that fails a pre-determined criteria, to obtain identified second image portions;
    calculating, for each identified second image portion, an interpolated deformation vector in accordance with deformation vectors of neighbour second image portions;
    substituting, for each identified second image portion, its deformation vector with its corresponding interpolated deformation vector; and
    registering second image portions to their corresponding first image portions in accordance with deformation vectors that pass the pre-determined criteria and in accordance the interpolated deformation vectors.

4. The non-transitory computer-readable medium of claim 3 wherein calculating, for each identified second image portion, the interpolated deformation vector in accordance with the deformation vectors of the neighbour second image portions includes performing a bi-linear interpolation in accordance with the deformation vectors of the neighbour second image portions.

* * * * *